US00PP18222P2

(12) United States Plant Patent
Whetman

(10) Patent No.: US PP18,222 P2
(45) Date of Patent: Nov. 20, 2007

(54) ***DIANTHUS* PLANT NAMED 'DEVON ESTHER'**

(50) Latin Name: *Dianthus×hybrida*
Varietal Denomination: DEVON ESTHER

(76) Inventor: John Whetman, Deer Park Farm, Chudleigh, Devon TQ113ONH (GB)

( * ) Notice: Subject to any disclaimer, the term of this patent is extended or adjusted under 35 U.S.C. 154(b) by 59 days.

(21) Appl. No.: 11/274,010

(22) Filed: Nov. 14, 2005

(51) Int. Cl.
*A01H 5/00* (2006.01)

(52) U.S. Cl. ..... Plt./272

(58) Field of Classification Search ..... Plt./272
See application file for complete search history.

*Primary Examiner*—Kent Bell
*Assistant Examiner*—S. B. McCormick-Ewoldt

(57) ABSTRACT

A new cultivar of *Dianthus* plant named 'DEVON ESTHER' that is characterized by pronounced compact habit, grey-green foliage, and soft magenta flowers. In combination these traits set 'DEVON ESTHER' apart from all other existing varieties of *Dianthus* known to the inventor.

2 Drawing Sheets

Genus: *Dianthus*. Species: ×*hybrida*.
Denomination: 'DEVON ESTHER'.

BACKGROUND OF THE INVENTION

The present invention relates to a new and distinct cultivar of carnation that is grown for use as a flowering plant for pots and containers. The new cultivar is known botanically as *Dianthus×hybrida* and will be referred to hereinafter by the cultivar name 'DEVON ESTHER'.

'DEVON ESTHER' is a complex hybrid plant that is the product of a breeding program started by the inventor in 1980. The breeding program is ongoing, conducted in a cultivated area of Houndspool, Dawlish, Devon, United Kingdom. The primary focus of the breeding program is to produce new cultivars of carnations that exhibit unique growth habit. The inventor selected 'DEVON ESTHER' in 2001 for its unique pronounced compact habit accompanied by abundant soft magenta flowers that bloom from May through October.

'DEVON ESTHER' is a dwarf carnation exhibiting pronounced compact habit, grey-green foliage, and soft magenta flowers. The colors of stems, leaves, calyx, and epicalyx are of material retaining the characteristic waxy bloom of *Dianthus*. 'DEVON ESTHER' resulted from the open pollination between two unknown varieties of *Dianthus*.

The variety of *Dianthus* which is considered by the inventor to most closely resemble 'DEVON ESTHER' is the inventor's variety *Dianthus* 'Devon Winnie' (U.S. Plant Pat. No. 14,893). When compared with these two varieties, the vigor of 'DEVON ESTHER' is greater than 'Devon Winnie'. 'DEVON ESTHER' exhibits a softer and more purple flower than 'Devon Winnie'. 'DEVON ESTHER' has a stronger perfume than the moderately perfumed 'Devon Winnie'.

Asexual reproduction of the new cultivar was first accomplished by the inventor in 2001 in a cultivated area of Houndspool, United Kingdom. The method of asexual propagation used was vegetative cuttings. Since that time the characteristics of the new cultivar have been determined stable and are reproduced true to type in successive generations of asexual reproduction.

SUMMARY OF THE INVENTION

The following traits have been repeatedly observed and represent the characteristics of the new *Dianthus* cultivar 'DEVON ESTHER'. These traits in combination distinguish this cultivar from all other commercial varieties known to the inventor. 'DEVON ESTHER' has not been tested under all possible conditions and phenotypic differences may be observed with variations in environmental, climatic and cultural conditions, however, without any variance in genotype.

1. *Dianthus* 'DEVON ESTHER' exhibits a pronounced compact habit.
2. *Dianthus* 'DEVON ESTHER' blooms profusely.
3. *Dianthus* 'DEVON ESTHER' exhibits soft magenta flowers from May through October.
4. *Dianthus* 'DEVON ESTHER' exhibits grey-green foliage.
5. At maturity, the height of the foliage mound of *Dianthus* 'DEVON ESTHER' is 15 cm–20 cm. The mature width is approximately 10 cm–15 cm.
6. *Dianthus* 'DEVON ESTHER' is a perennial herb.
7. *Dianthus* 'DEVON ESTHER' is suitable for use as a flowering plant in pots and containers.
8. *Dianthus* 'DEVON ESTHER' is hardy to minus 15° Centigrade.

BRIEF DESCRIPTION OF THE DRAWINGS

The accompanying color drawings illustrate the overall appearance of the new *Dianthus* variety 'DEVON ESTHER' showing colors as true as it is reasonably possible to obtain in colored reproductions of this type. Colors in the drawings may differ from the color values cited in the detailed botanical description, which accurately describe the actual colors of the new variety 'DEVON ESTHER'.

The drawing labeled as FIG. 1 depicts an entire flowering plant.

Figure 1:
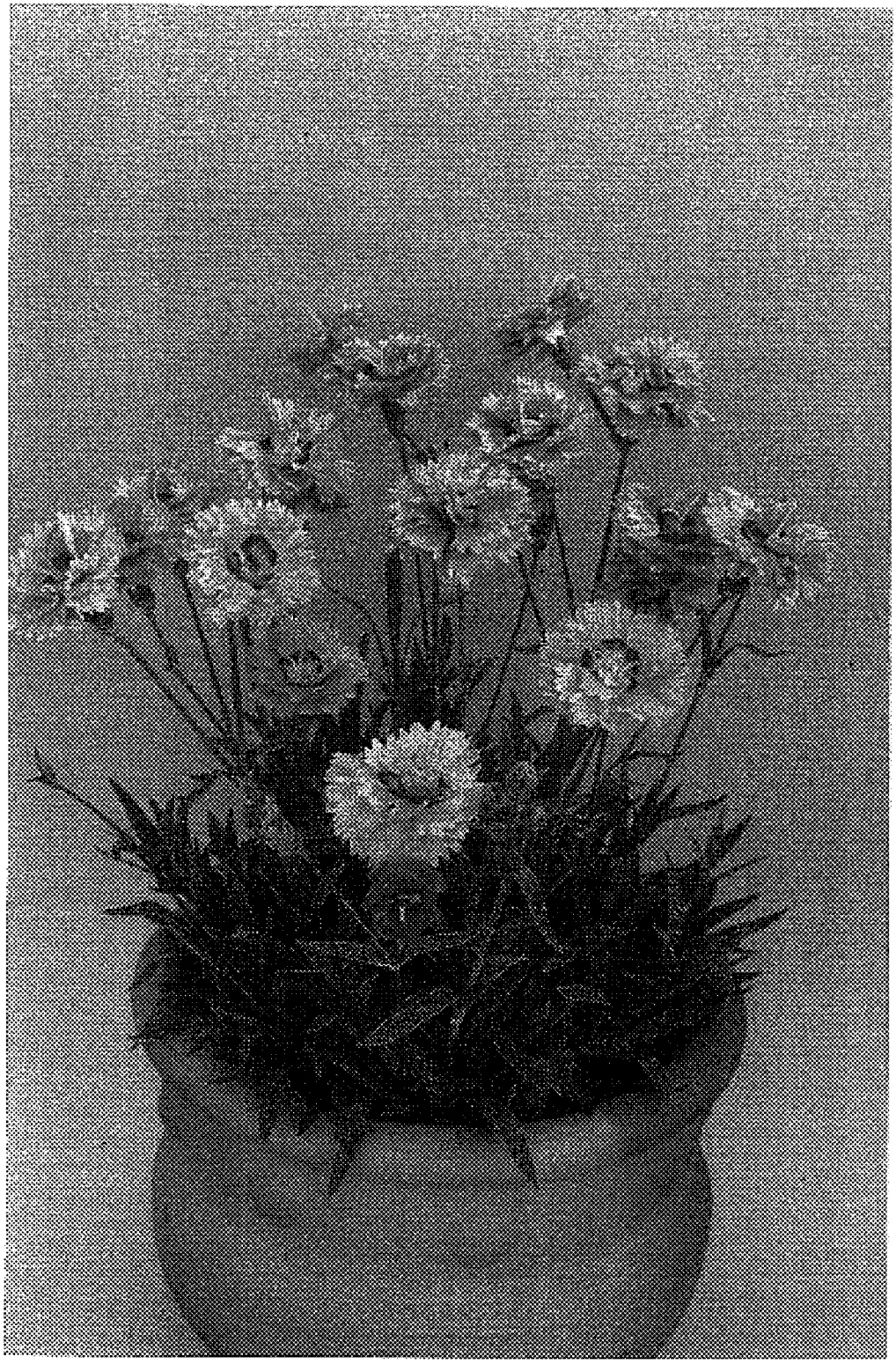
Figure 2:
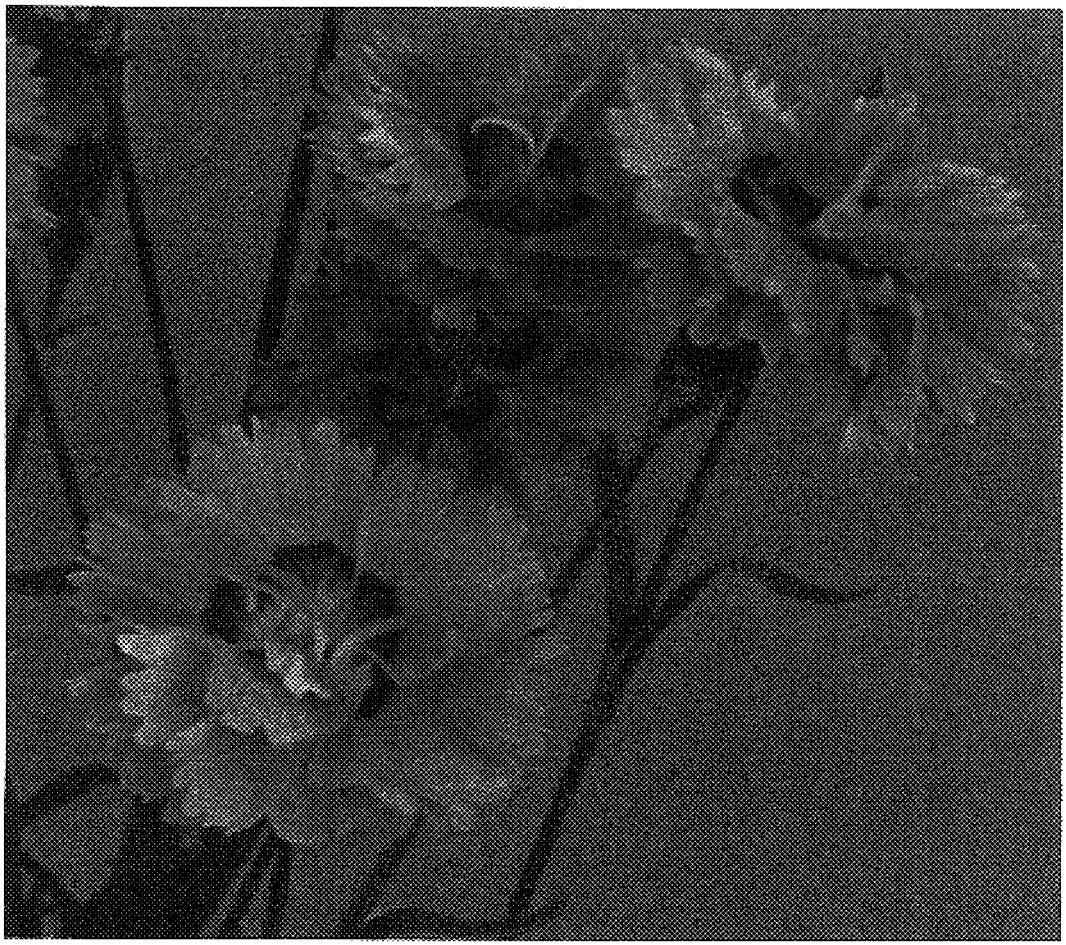

The drawing labeled as FIG. 2 depicts a close-up view of the flower.

All drawings were made from 12 months old plants which had been grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'DEVON ESTHER'. Data was collected in spring from 1.5-liter container plants which had been grown for 12 months in an unheated greenhouse in Devon, United Kingdom. The color determinations are in accordance with the 2001 edition of The Royal Horticultural Society Colour Chart except where general color terms of ordinary dictionary significance are used. No chemicals were used to treat the plants. Growing conditions are typical to other *Dianthus*.

Botanical classification: *Dianthus* 'DEVON ESTHER'.
Species: ×*hybrida*.
Common name: Dwarf carnation.
Commercial classification: *DianThus* hybrid.
Type: Perennial herb.
Use: Used as a flowering plant for pots and containers.
Parentage: 'DEVON ESTHER' is a complex hybrid plant that resulted from open pollination between two unknown varieties of *Dianthus*.
Plant description:
- *Bloom period.*—May through October.
- *Plant habit.*—Pronounced compact habit.
- *Plant height.*—15 cm–20 cm. in height at maturity.
- *Plant width.*—10 cm–15 cm in width at maturity.
- *Plant hardiness.*—Hardy to minus 15° Centigrade.
- *Root system.*—Fine fibrous roots.
- *Propagation.*—Propagation is accomplished using vegetative cuttings.
- *Cultural requirements.*—Grow in full sun, with moderate water, and well-drained moderately fertile soil.
- *Diseases and pests.*—Susceptible to known *Dianthus* pests and disease but no other susceptibilities to pests or disease are known to the inventor.
- *Time and temperature needed to produce a rooted cutting.*—2 weeks are needed to produce roots on cuttings using a mist propagation unit with bottom heat of 21° Centigrade, and a minimum air temperature of 15° Centigrade.
- *Crop time.*—An average of 3 months in the spring and 6 months in the fall are needed to produce a finished container size plant from a well-rooted cutting.

Stem:
- *Shape.*—Cylindrical.
- *Stem dimensions.*—80 mm–90 mm. in length and 3 mm. in diameter.
- *Stem surface.*—Glabrous and glaucous.
- *Stem color.*—136A.
- *Branching.*—Numerous basal breaks.
- *Internode length.*—10 mm–12 mm between nodes.
- *Node color.*—145D.
- *Node dimensions.*—4 mm. in diameter and 3 mm. in length.

Foliage: Loose cushion of grass-like glaucous leaves.
Leaf:
- *Type.*—Simple.
- *Shape.*—Linear.
- *Apex.*—Acute.
- *Base.*—Decurrent.
- *Venation.*—Not Prominent.
- *Margins.*—Entire.
- *Attachment.*—Sheathing.
- *Arrangement.*—Opposite and spiraling up stem.
- *Surfaces* (*adaxial and abaxial*).—Glaucous.
- *Leaf dimensions.*—35 mm in length and an average of 4 mm in width.
- *Leaf color* (*adaxial surfaces*).—N136A.
- *Leaf color* (*abaxial surfaces*).—N136B.
- *Fragrance.*—Absent.

Flowers:
- *Inflorescence.*—Cymose.
- *Number of flowers per stem.*—From 3 to 5.
- *Flower type.*—Salviform, double and symmetrical.
- *Flower length.*—(Pedicel, including calyx): 35 mm.
- *Flower diameter.*—40 mm.
- *Fragrance.*—Present, strongly clove-like.
- *Bud color.*—Each bud is N138C on apical half and 13A on basal half.
- *Anthocyanin.*—When present 137C.
- *Bud dimensions.*—20 mm in length and 8 mm in width.
- *Bud shape.*—Cylindrical.
- *Petals.*—Persistent, double, overlapping and sympetalous.
- *Petal number.*—13 to 15 often with 5 petaloid stamens.
- *Petal margin.*—Slightly dentate (toothed 3 mm deep).
- *Petal shape.*—Obdeltoid and slightly folded.
- *Petal surface.*—Glabrous.
- *Petal dimensions.*—35 mm in length and 25 mm in width.
- *Petal color* (*adaxial surface*).—Petal consists of rounded blade with strap-like base. Ground color of blade: N78C. Color of band in center of blade: N79C. Strap: 145D.
- *Calyx dimensions.*—8 mm. in diameter and 18 mm in length.
- *Calyx color.*—N137C.
- *Anthocyanin.*—Absent.
- *Sepal number.*—5 in number.
- *Fused or unfused.*—Fused.
- *Color.*—133B.
- *Peduncle.*—Dimensions: 150 mm in length and 2 mm in diameter. Color: N138C. Suface: Glaucous.
- *Bracts.*—Epicalyx bracts: 1 pair (2 individual bracts). Shape of outer lobe: acuminate. Dimensions: 7 mm wide, 6 mm long. Color: 137C. Anthocyanin: absent.
- *Bracteoles.*—Number: 1 pair (2 individual bracts). Dimensions: 3 mm wide, 5 mm long. Anthocyanin: absent.
- *Stipules.*—Number: Two per node. Dimensions: A range of 3 mm to 5 mm in width, and a range of 7 mm to 35 mm in length. Color: 139C.
- *Lastingness of the flower.*—15 days at 20° C.

Reproductive organs:
- *Stamens.*—Variable or malformed.
- *Stamen dimensions.*—5 mm to 15 mm in length and 0.5 mm in diameter.
- *Stamen color.*—147C.
- *Anther number.*—Usually absent.
- *Pollen.*—Absent.

*Amount of pollen.*—When present the amount is moderate.

*Pollen color.*—When pollen is present the color ranges from 155A to N74D.

*Pistil.*—One that divides into two above the ovary.

*Pistil dimensions.*—37 mm in length.

*Styles.*—Two in number.

*Style dimensions.*—25 mm in length and 1 mm. in diameter.

*Style color.*—Upper half N74D, lower half white.

*Stigma number.*—Two in number.

*Stigma shape.*—Undivided.

*Color of stigma.*—N74D.

*Height above petals.*—5 mm. above petals.

*Ovary position.*—Superior.

*Ovary dimensions.*—12 mm in length and 4 mm in diameter.

*Ovary shape.*—Spindle shaped.

*Ovary color.*—144C.

Seed:

*Seed.*—Absent.

It is claimed:

1. A new and distinct cultivar of *Dianthus* plant named 'DEVON ESTHER' as described and illustrated herein.

* * * * *